(12) United States Patent
Ishihara et al.

(10) Patent No.: US 9,024,103 B2
(45) Date of Patent: May 5, 2015

(54) METHOD FOR PRODUCING OLEFIN

(75) Inventors: Daisuke Ishihara, Wakayama (JP);
Nobuyoshi Suzuki, Wakayama (JP);
Hideo Tahara, Wakayama (JP); Hiroshi Danjo, Wakayama (JP)

(73) Assignee: Kao Corporation, Tokyo (JP)

( * ) Notice: Subject to any disclaimer, the term of this patent is extended or adjusted under 35 U.S.C. 154(b) by 23 days.

(21) Appl. No.: 13/509,437

(22) PCT Filed: Nov. 10, 2010

(86) PCT No.: PCT/JP2010/069989
§ 371 (c)(1),
(2), (4) Date: May 11, 2012

(87) PCT Pub. No.: WO2011/058990
PCT Pub. Date: May 19, 2011

(65) Prior Publication Data
US 2012/0226085 A1     Sep. 6, 2012

(30) Foreign Application Priority Data
Nov. 12, 2009 (JP) .................................. 2009-258512

(51) Int. Cl.
C07C 1/207  (2006.01)
C07C 1/20   (2006.01)
C07C 1/22   (2006.01)
C07C 1/24   (2006.01)

(52) U.S. Cl.
CPC .................................... C07C 1/2078 (2013.01)

(58) Field of Classification Search
CPC ....................................................... C07C 1/207
USPC .................................................. 585/638, 639
See application file for complete search history.

(56) References Cited

U.S. PATENT DOCUMENTS 3,530,198 A * 9/1970 Fenton .......................... 585/357
5,077,447 A * 12/1991 Miller et al. .................. 585/638
2011/0190564 A1   8/2011 Suzuki et al.

FOREIGN PATENT DOCUMENTS

| JP | 56 40616    | 4/1981 |
| JP | 2009 173611 | 8/2009 |
| JP | 2010 168340 | 8/2010 |
| WO | 2010 024420 | 3/2010 |

OTHER PUBLICATIONS

Goossen, L.J., et al., "A mild and efficient protocol for the conversion of carboxylix acids to olefins by a catalytic decarbonylative elimination reaction," Chemical Communications, No. 6, pp. 724-725, (2004).
Foglia, T.A., et al., "Decarbonylation Dehydration of Fatty Acids to Alkenes in the Presence of Transition Metal Complexes," Journal of the American Chemists' Society, vol. 53, pp. 737-741, (Dec. 1976).
International Search Report Issued Dec. 7, 2010 in PCT/JP10/69989 Filed Nov. 10, 2010.
International Preliminary Report on Patentability and Written Opinion issued Jun. 12, 2012 in Application No. PCT/JP2010/069989 (English Translation).
U.S. Appl. No. 13/976,706, filed Jun. 27, 2013, Suzuki, et al.

* cited by examiner

*Primary Examiner* — In Suk Bullock
*Assistant Examiner* — Youngsul Jeong
(74) *Attorney, Agent, or Firm* — Oblon, McClelland, Maier & Neustadt, L.L.P.

(57) ABSTRACT

The present invention provides a method for producing an olefin from a carboxylic acid having a β-hydrogen atom or an anhydride thereof in the presene of a catalyst containing at least one metal element selected from metals of Group 8, Group 9 and Group 10 and bromine element at a reaction temperature of 120° C. to 270° C.

19 Claims, No Drawings

METHOD FOR PRODUCING OLEFIN

CROSS REFERENCES TO RELATED APPLICATIONS

This application is a 371 of International Patent Application No. PCT/JP10/069989, filed on Nov. 10, 2010, and claims priority to Japanese Patent Application No. 2009-258512, filed on Nov. 12, 2009.

FIELD OF THE INVENTION

The present invention relates to a method for producing an olefin from a carboxylic acid having a β-hydrogen atom or an anhydride thereof, and more particularly to a method for producing an olefin suitably used as an intermediate for base materials such as a surfactant.

BACKGROUND OF THE INVENTION

There are known methods for producing an olefin from a carboxylic acid by a catalytic reaction, including a method of production from an acid anhydride with a catalyst containing an element selected from Group 8, Group 9, and Group 10 metals and copper (U.S. Pat. No. 5,077,447), a method of production with a Pd or Rh complex catalyst at a reaction temperature of 280° C. (J. Am. Oil. Chem. Soc., 1976, 53, 737), and a method of production using a polar solvent (dimethylpropyleneurea (DMPU) or the like) and pivalic anhydride together with a Pd complex catalyst at a reaction temperature of 110° C. (Chem. Commun., 2004, 724).

JP-A2009-173611 discloses a method for producing a branched β-alcohol from a saturated carboxylic acid in the presence of a copper-containing catalyst.

JP-A2010-168340, filed on Aug. 5, 2010, (corresponding to WO-A2010/024420, published on Mar. 4, 2010) discloses a method for producing an olefin from a carboxylic acid having a β-hydrogen atom or a derivative thereof in the presence of a catalyst.

SUMMARY OF THE INVENTION

The present invention provides a method for producing an olefin from a carboxylic acid having a β-hydrogen atom or an anhydride thereof in the presence of a catalyst, wherein the catalyst contains at least one metal element selected from Group 8 metals, Group 9 metals and Group 10 metals and bromine element and a reaction temperature is 120° C. to 270° C.

DETAILED DESCRIPTION OF THE INVENTION

Although methods described in U.S. Pat. No. 5,077,447, J. Am. Oil. Chem. Soc., 1976, 53, 737, and Chem. Commun., 2004, 724 can produce an intended olefin from a carboxylic acid by a catalytic reaction, these methods have problems of a low yield of the olefin (U.S. Pat. No. 5,077,447), a short catalyst lifetime and a low olefin selectivity due to the high reaction temperature in order to enhance a catalytic activity (J. Am. Oil. Chem. Soc., 1976, 53, 737), and needs of the special solvent and the additive in order to increase an olefin selectivity (Chem. Commun., 2004, 724).

The present invention provides the method that can selectively produce an intended olefin at high yield without requiring a special solvent and an additive.

The present inventors have studied about a ligand in a metal complex catalyst and reaction conditions, and accomplished the present invention by conducting the reaction with a catalyst containing a specific metal element together with a bromine element at a specific reaction temperature.

According to the production method of the present invention, an olefin suitably used as an intermediate for base materials such as a surfactant can be selectively produced at high yield by the reaction at lower temperature without requiring a special solvent and an additive.

Any carboxylic acid having a β-hydrogen atom or an anhydride thereof can be used in the present invention if it has at least one hydrogen atom at β-position of a carbonyl group. The carboxylic acid or an anhydride thereof may be of a saturated or an unsaturated type, may have a partially cyclic form, may contain a heteroatom, and may have plural carbonyl groups. Preferred are saturated monocarboxylic acids and anhydrides thereof, and more preferred are aliphatic carboxylic acids having a β-hydrogen atom and anhydrides thereof.

Specific examples of the carboxylic acid having a β-hydrogen atom include caproic acid, caprylic acid, capric acid, lauric acid, myristic acid, palmitic acid, stearic acid, behenic acid, 3-phenylpropionic acid, adipic acid, azelaic acid, eicosanoic acid, 9-decenoic acid, 10-undecenoic acid, oleic acid, 2,4-hexadienoic acid, 3-methylbutanoic acid, 6-octadecynoic acid, hydnocarpic acid, gorlic acid, and ricinolic acid.

Specific examples of the carboxylic anhydride having a β-hydrogen atom include caproic anhydride, caprylic anhydride, capric anhydride, lauric anhydride, myristic anhydride, palmitic anhydride, stearic anhydride, behenic anhydride, 3-phenylpropionic anhydride, adipic anhydride, azelaic anhydride, eicosanoic anhydride, 9-decenoic anhydride, 10-undecenoic anhydride, oleic anhydride, 2,4-hexadienoic anhydride, 3-methylbutanoic anhydride, 6-octadecynoic anhydride, hydnocarpic anhydride, gorlic anhydride, ricinolic anhydride, succinic anhydride, and the like, or a condensed anhydride of formic acid, acetic acid, propionic acid, butyric acid or a carboxylic acid having a β-hydrogen atom, shown above, and another carboxylic acid having a β-hydrogen atom, shown above.

For the carboxylic acid having a β-hydrogen atom and the anhydride of the present invention, the carboxylic acid is represented by the formula (i) in which $R^1$ preferably has 2 to 30 carbon atoms, more preferably 9 to 21 carbon atoms, and even more preferably 11 to 17 carbon atoms. The carboxylic anhydride is represented by the formula (ii) in which at least one of $R^1$ and $R^2$ preferably has 2 to 29 carbon atoms, more preferably 8 to 21 carbon atoms, and even more preferably 11 to 17 carbon atoms. In two formulae, $R^1$ preferably represents a saturated or unsaturated hydrocarbon group having a β-hydrogen atom and 11 to 17 carbon atoms, and $R^2$ preferably represents a hydrogen atom or a saturated or unsaturated hydrocarbon group having 1 to 17 carbon atoms.

The catalyst used in the present invention contains at least one metal element selected from the group consisting of Group 8, Group 9 and Group 10 metals together with a bromine element. Examples of the catalyst containing at least one metal element selected from the group consisting of Group 8, Group 9 and Group 10 metals together with a bromine element include compounds containing at least one metal element selected from the group consisting of Group 8, Group 9 and Group 10 metals, which element is coordinated with a bromine element (hereinafter, referred to as catalyst A), and mixtures of compounds containing at least one metal element selected from the group consisting of Group 8, Group 9 and Group 10 metals with bromides (hereinafter, referred to as catalyst B). The at least one metal element selected from the group consisting of Group 8, Group 9 and Group 10 metals is preferably Fe, Ru, Os, Co, Rh, Ir, Ni, Pd, and Pt, more preferably Fe, Ru, Co, Rh, Ir, Ni, and Pt, and even more preferably Fe, Rh, and Ni.

The catalyst A is preferably a compound in which only at least one bromine element coordinates with at least one metal element selected from Group 8 metals, Group 9 metals and Group 10 metals, or a compound in which at least one bromine element and further at least one ligand selected from a pyridyl ligand, a organophosphorous ligand and a carbonyl ligand coordinate with the metal element. Examples of the catalyst A include $FeBr_2$, $CoBr_2$, $[Rh(CO)_2Br]_2$, $RhBr_3 \cdot nH_2O$, $IrBr(CO)(PPh_3)_2$, $NiBr_2$, $Ni(PPh_3)_2Br_2$, $PtBr_2$, and $Pt(PPh_3)_2Br_2$ (wherein, Ph represents a phenyl group, the same applies below). Among these compounds, preferred are $FeBr_2$, $[Rh(CO)_2Br]_2$, $RhBr_3 \cdot nH_2O$, and $NiBr_2$.

These catalysts may be used together with a ligand compound, such as N-heterocyclic carbene compounds, pyridine compounds such as 2,2-bipyridyl and pyridine, oxygene-containing compounds or organophosphorous compounds. Preferred are, if used, organophosphorous compounds. Examples of the organophosphorous compound include dimethylphenylphosphine, diethylphenylphosphine, methyldiphenylphosphine, ethyldiphenylphosphine, cyclohexyldiphenylphosphine, tricyclohexylphosphine, triisopropylphosphine, tributylphosphine, tri-t-butylphosphine, tribenzylphosphine, triphenylphosphine, tris(paramethoxyphenyl)phosphine, and 1,2-bis(diphenylphosphino)ethane. Preferred are triphenylphosphine and 1,2-bis(diphenylphosphino)ethane. These ligand compounds may be used alone or in combination.

For achieving good stability and reaction rate of the catalyst, an amount of the ligand compound is preferably 0.1 to 1000 mol, more preferably 0.2 to 500 mol, and even more preferably 0.3 to 100 mol to one mole of metal atom of Group 8, Group 9 and Group 10 metals, based on the element selected from Group 8, Group 9 and Group 10 metals.

An amount of the catalyst A is preferably 0.00001 to 0.2 mol, more preferably 0.0001 to 0.05 mol, and even more preferably 0.001 to 0.04 mol of the metal atom therein to one mole of the carboxylic acid having a β-hydrogen atom or an anhydride thereof.

The compound used in the catalyst B, containing at least one metal element selected from metals of Group 8, Group 9 and Group 10, is preferably a compound in which at least one ligand selected from chlorine atom, pyridyl ligands, organophosphorous ligands and carbonyl ligands coordinates with at least one metal element selected from metals of Group 8, Group 9 and Group 10. Specific examples of the compound include $[Rh(CO)_2Cl]_2$, $(Ph_3P)_2Rh(CO)Cl$, $(Ph_3P)_3RhCl$, $(Ph_3P)_2NiCl_2$, $CoCl_2$, $(Ph_3P)_2PdCl_2$, $(Ph_3P)_4Pd$, $Pd(OAc)_2$, $(Ph_3P)_2CoCl_2$, $CoCl_3$, $(Ph_3P)_2PtCl_2$, $FeCl_2$, $Ru_3(CO)_{12}$, $[Ru(CO)_3Cl_2]_2$, $(Ph_3P)_3RuCl_2$, $(Ph_3P)_4RuCl_2$, $(Ph_3P)_2Ir(CO)Cl$, $IrCl(CO)_3$, and $(Ph_3P)_3CuCl$. Preferred are $[Rh(CO)_2Cl]_2$, $IrCl(CO)_3$, $(Ph_3P)_2NiCl_2$, $Ru_3(CO)_{12}$, $CoCl_2$, $(Ph_3P)_2PtCl_2$, $FeCl_2$, and more preferred are $[Rh(CO)_2Cl]_2$, $FeCl_2$, and $(Ph_3P)_2NiCl_2$.

These compounds maybe used together with ligand compounds, such as N-heterocyclic carbene compounds, pyridine compounds, such as 2,2-bipyridyl and pyridine, oxygene-containing compounds or organophosphorous compounds. Preferred are, if used, organophosphorous compounds. Specific examples of the organophosphorous compound are as described for the catalyst A.

The bromide used in the catalyst B can be of any kind. Examples of the bromide include bromides of the element selected from Group 1 to Group 7 and Group 11 to Group 14 elements and quaternary ammonium compounds represented by the formula (1):

$$[R—(Y)_n]_4N^+Br^- \quad (1)$$

wherein, R represents a hydrogen atom or a hydrocarbon group having 1 to 22 carbon atoms; Y represents a group —Z—$(CH_2)_m$—, in which Z represents an ether group, an amino group, an amide group or an ester group, and more specifically —O—, —NH—, —CONH—, —NHCO—, —COO—, or —OCO—, and m represents a number of 1 to 6; n represents a number of 0 or 1; plural R's, plural Y's, and plural n's each may be the same as or different from one another, and [R—$(Y)_n$] may, together with itself, form a cyclic structure.

The quaternary ammonium compound of the formula (1) preferably has R representing an alkyl group having 1 to 7 carbon atoms or a benzyl group (preferably an alkyl group having 1 to 7 carbon atoms) and n representing 0, and is more preferably $Et_4N^+Br^-$ or $(n\text{-Butyl})_4N^+Br^-$ (wherein, Et represents an ethyl group, and n-Butyl represents an n-butyl group), and particularly preferably $Et_4N^+Br^-$.

The bromide used in the catalyst B is preferably bromides of the element selected from Group 1, Group 11, and Group 12 elements, more preferably bromides selected from Group 1 element, and even more preferably NaBr and KBr.

An amount of the catalyst B is adjusted such that an amount of the compound containing at least one metal element selected from the group consisting of Group 8, Group 9, and Group 10 metals is preferably 0.00001 to 0.2 mol, more preferably 0.0001 to 0.05 mol, and even more preferably 0.001 to 0.03 mol of the metal atom therein to one mole of the carboxylic acid having a β-hydrogen atom or an anhydride thereof, and an amount of the bromide is preferably 0.001 to 10 mol, more preferably 0.03 to 3 mol, and even more preferably 0.05 to 2 mol to one mole of the carboxylic acid or an anhydride thereof.

In the present invention, for dissolving the catalyst and/or a starting material, a solvent may be used. From the viewpoint of reaction efficiency, a weight ratio of starting material/ (starting material+solvent) is preferably 1/26 to 1/1, more preferably 1/5 to 1/1, and even more preferably 1/2 to 1/1.

Any solvent can be used if it does not affect the reaction adversely. Examples of the solvent include aromatic hydrocarbons such as dodecylbenzene, aliphatic hydrocarbons such as squalane, alicyclic hydrocarbons such as cyclodecane, alcohols such as ethylene glycol, ethers such as ethylene glycol dimethyl ether, maleic anhydride, phthalic anhydride, acetic anhydride, and acetic acid.

In the present invention, on one hand, from the viewpoint of reaction rate, the reaction temperature is preferably high, more preferably not less than 120° C., more preferably not less than 140° C., and even more preferably not less than 150° C. On the other hand, from the viewpoints of catalyst lifetime and olefin selectivity, the reaction temperature is preferably low, more preferably not more than 270° C., more preferably not more than 260° C., and even more preferably not more than 250° C.

From the viewpoint of reaction rate, the pressure in the reaction is preferably 1 to 300 kPa, more preferably 5 to 150 kPa, and even more preferably 25 to 110 kPa.

An olefin produced by the production method of the present invention may have a terminal double bond or may be an isomer thereof, an internal olefin having a double bond at an internal position.

The olefin produced by the method of the present invention can be suitably used as an intermediate for base materials such as a surfactant.

EXAMPLES

The following Examples demonstrate the present invention. Examples are intended to illustrate the present invention and not to limit the present invention.

Unless otherwise stated, "%" refers to "% by mole".

Example 1a

In a 50 mL recovery flask containing a stirring bar, 4.27 g (15.0 mmol) of stearic acid (Kao Corporation, LUNAC S98), 32.8 mg (0.15 mmol) of $NiBr_2$ (SIGMA ALDRICH), and 157.4 mg (0.6 mmol) of triphenylphosphine ($PPh_3$) (SIGMA ALDRICH) were added. The inner atmosphere was replaced with nitrogen. The mixture was stirred at 250° C. under 0.03 MPa of nitrogen. Three hours later, heating stopped, to the mixture was added 33.3 mg of anisole (SIGMA ALDRICH) as an internal standard. The mixture was analyzed with a $^1$H-NMR apparatus (Varian Inc., MERCURY400) (Integrals of the signals of vinyl protons of a terminal olefin, vinyl protons of an internal olefin and methyl group of anisole were compared to quantify the amounts of the starting material and products. These amounts were used to calculate a conversion rate of the starting material, an olefin selectivity, and yields of olefins).

A conversion rate of stearic acid was 14% and yields of a terminal olefin and an internal olefin were 1% and 4%, respectively, to the starting stearic acid.

Example 1b

This example was conducted in the same way as Example 1a, except that 4.27 g of squalane (SIGMA ALDRICH) was added as a solvent.

A conversion rate of stearic acid was 5%, yields of a terminal olefin and an internal olefin were 0% and 5% to the starting stearic acid, respectively.

Comparative Example 1a

This example was conducted in the same way as Example 1a, except that $NiCl_2$ (SIGMA ALDRICH) was used instead of $NiBr_2$.

A conversion rate of stearic acid was 10%, yields of a terminal olefin and an internal olefin were 0% and 1% ,o the starting stearic acid, respectively.

Comparative Example 1b

This example was conducted in the same way as Example 1a, except that the reaction temperature was 280° C. instead of 250° C.

A conversion rate of stearic acid was 22%, yields of a terminal olefin and an internal olefin were 0% and 6% to the starting stearic acid, respectively.

Results of Examples 1a to 1b and Comparative Examples 1a to 1b are shown in Table 1.

TABLE 1

|  | Example | | Comparative example | |
|---|---|---|---|---|
|  | 1a | 1b | 1a | 1b |
| Kind of catalyst | $NiBr_2$ | $NiBr_2$ | $NiCl_2$ | $NiBr_2$ |
| Amount of catalyst (% by mole to stearic acid) | 1 | 1 | 1 | 1 |
| Amount of $PPh_3$ added (% by mole to stearic acid) | 4 | 4 | 4 | 4 |
| Squalane (solvent)/(stearic acid + squalane) (weight ratio) | 0 | 0.5 | 0 | 0 |
| Reaction temperature (° C.) | 250 | 250 | 250 | 280 |
| Conversion rate (%) | 14 | 5 | 10 | 22 |
| Olefin selectivity (%) | 36 | 100 | 10 | 27 |
| Total yield of olefins (%) | 5 | 5 | 1 | 6 |
| Yield of terminal olefin (%) | 1 | 0 | 0 | 0 |
| Yield of internal olefin (%) | 4 | 5 | 1 | 6 |

Both Examples 1a and 1b showed high olefin selectivity, compared with Comparative Examples 1a and 1b.

Example 2

In a 50 mL recovery flask containing a stirring bar, 4.27 g (15.0 mmol) of stearic acid (Kao Corporation, LUNAC S98), 17.5 mg (0.045 mmol) of $[Rh(CO)_2Cl]_2$ (SIGMA ALDRICH), 17.9 mg (0.045 mmol) of 1,2-bis(diphenylphosphino)ethane (DPPE) (SIGMA ALDRICH), and 1.785 g (15.0 mmol) of KBr (SIGMA ALDRICH) were added. The inner atmosphere was replaced with nitrogen. The mixture was stirred at 250° C. under 0.03 MPa of nitrogen. Three hours later, heating stopped, to the mixture was added 33.3 mg of anisole as an internal standard. The mixture was analyzed with a $^1$H-NMR apparatus (A yield of olefins was calculated in the same way as in Example 1a).

A yield of olefins was 5% to the starting stearic acid.

Comparative Example 2

This Example was conducted in the same way as Example 2, except that KBr was not added.

A yield of olefins was 1% to the starting stearic acid.

Results of Example 2 and Comparative Example 2 are shown in Table 2.

TABLE 2

|  | Example 2 | Comparative example 2 |
|---|---|---|
| Kind of catalyst | KBr + $[Rh(CO)_2Cl]_2$ | $[Rh(CO)_2Cl]_2$ |
| Amount of $[Rh(CO)_2Cl]_2$ (% by mole to stearic acid) | 0.3 | 0.3 |
| Amount of KBr (% by mole to stearic acid) | 100 | — |
| Amount of DPPE added (% by mole to stearic acid) | 0.3 | 0.3 |
| Reaction temperature (° C.) | 250 | 250 |
| Yield of olefin (%) | 5 | 1 |

Example 2 showed high yield of olefins, compared with Comparative Example 2.

Example 3

In a 50 mL recovery flask containing a stirring bar, 4.13 g (7.5 mmol) of stearic anhydride (Tokyo Chemical Industry, Co., Ltd.), 32.8 mg (0.15 mmol) of $NiBr_2$ (SIGMA ALDRICH), and 157.4 mg (0.6 mmol) of $PPh_3$ (SIGMA ALDRICH) were added. The inner atmosphere was replaced with nitrogen. The mixture was stirred at 200° C. under 0.03 MPa of nitrogen. Three hours later, heating stopped, to the mixture was added 33.3 mg of anisole as an internal standard. The mixture was analyzed with a $^1$H-NMR apparatus (A conversion rate of the starting material, an olefin selectivity, and yields of olefins were calculated in the same way as in Example 1a).

A conversion rate of stearic anhydride was 64%, yields of a terminal olefin and an internal olefin were 29% and 25% to the starting stearic anhydride, respectively.

Comparative Example 3

This Example was conducted in the same way as Example 3, except that $NiCl_2$ was used instead of $NiBr_2$.

The reaction never progressed, and a conversion rate of stearic anhydride was 0%.

Example 4

This Example was conducted in the same way as Example 3, except that $RhBr_3 \cdot nH_2O$ (Wako Pure Chemical Industries, Ltd.) was used instead of $NiBr_2$.

A conversion rate of stearic anhydride was 37%, yields of a terminal olefin and an internal olefin were 28% and 2% to the starting stearic anhydride, respectively.

Comparative Example 4

This Example was conducted in the same way as Example 4, except that $RhCl_3 \cdot nH_2O$ (SIGMA ALDRICH) was used instead of $RhBr_3 \cdot nH_2O$.

The reaction never progressed, and a conversion rate of stearic anhydride was 0%.

Example 5

This Example was conducted in the same way as Example 3, except that $FeBr_2$ (SIGMA ALDRICH) was used instead of $NiBr_2$, and the reaction temperature was 250° C. instead of 200° C.

A conversion rate of stearic anhydride was 11%, yields of a terminal olefin and an internal olefin were 2% and 4% to the starting stearic anhydride, respectively.

Comparative Example 5

This Example was conducted in the same way as Example 5, except that $FeCl_2$ (SIGMA ALDRICH) was used instead of $FeBr_2$.

A conversion rate of stearic anhydride was 24%, yields of a terminal olefin and an internal olefin were 1% and 1% to the starting stearic anhydride, respectively.

Example 6

In a 50 mL recovery flask containing a stirring bar, 4.13 g (7.5 mmol) of stearic anhydride and 31.7 mg (0.05 mmol) of $[Rh(CO)_2Br]_2$ (prepared by a similar method as described in Maitlis. P.M.J. Organomet. Chem. 1990, 398, 311) were added. The inner atmosphere was replaced with nitrogen. The mixture was stirred at 160° C. under 0.03 MPa of nitrogen. Three hours later, heating stopped, to the mixture was added 33.3 mg of anisole as an internal standard. The mixture was analyzed with a $^1$H-NMR apparatus (A conversion rate of the starting material, an olefin selectivity, and yields of olefins were calculated in the same way as in Example 1a).

A conversion rate of stearic anhydride was 11%, yields of a terminal olefin and an internal olefin were 3% and 8% to the starting stearic anhydride, respectively.

Comparative Example 6a

This Example was conducted in the same way as Example 6, except that $[Rh(CO)_2Cl]_2$ was used instead of $[Rh(CO)_2Br]_2$.

The reaction didn't at all proceed and a conversion rate of stearic anhydride was 0%.

Comparative Example 6b

This Example was conducted in the same way as Example 6, except that the reaction temperature was 100° C. instead of 160° C.

A conversion rate of stearic anhydride was 6%, but a terminal olefin and an internal olefin were not produced.

Results of Examples 3 to 6 and Comparative Examples 3 to 6b are shown in Table 3.

TABLE 3

| | Example | | | | Comparative example | | | | |
|---|---|---|---|---|---|---|---|---|---|
| | 3 | 4 | 5 | 6 | 3 | 4 | 5 | 6a | 6b |
| Kind of catalyst | $NiBr_2$ | $RhBr_3 \cdot nH_2O$ | $FeBr_2$ | $[Rh(CO)_2Br]_2$ | $NiCl_2$ | $RhCl_3 \cdot nH_2O$ | $FeCl_2$ | $[Rh(CO)_2Cl]_2$ | $[Rh(CO)_2Br]_2$ |
| Amount of catalyst (% by mole to stearic anhydride) | 2 | 2 | 2 | 0.66 | 2 | 2 | 2 | 0.66 | 0.66 |
| Amount of added $PPh_3$ (% by mole to stearic anhydride) | 8 | 8 | 8 | — | 8 | 8 | 8 | — | — |
| Reaction temperature (° C.) | 200 | 200 | 250 | 160 | 200 | 200 | 250 | 160 | 100 |
| Conversion rate (%) | 64 | 37 | 11 | 11 | 0 | 0 | 24 | 0 | 6 |
| Olefin selectivity (%) | 84 | 81 | 55 | 100 | 0 | 0 | 8 | 0 | 0 |
| Total yield of olefins (%) | 54 | 30 | 6 | 11 | 0 | 0 | 2 | 0 | 0 |
| Yield of terminal olefin (%) | 29 | 28 | 2 | 3 | 0 | 0 | 1 | 0 | 0 |
| Yield of internal olefin (%) | 25 | 2 | 4 | 8 | 0 | 0 | 1 | 0 | 0 |

All Examples 3 to 6 showed high yield of olefin and high olefin selectivity, compared with Comparative Examples 3 to 6b.

The invention claimed is:

1. A method for producing an olefin, comprising converting a carboxylic acid having a β-hydrogen atom or an anhydride thereof to an olefin in the presence of a catalyst, at a reaction temperature of 120° C. to 270° C., wherein said catalyst is selected from the group consisting of $NiBr_2$, $RhBr_3$, $FeBr_2$, $[Rh(CO)_2Br]_2$, and a mixture of KBr and $[Rh(CO)_2Cl]_2$.

2. The method for producing an olefin according to claim 1, wherein said catalyst is selected from the group consisting of $NiBr_2$, $RhBr_3$, and $FeBr_2$.

3. The method for producing an olefin according to claim 2, wherein said catalyst is $NiBr_2$ and an amount of said $NiBr_2$ is 0.00001 to 0.2 mol as Ni to one mole of the carboxylic acid having a β-hydrogen atom or an anhydride thereof.

4. The method for producing an olefin according to claim 2, wherein said catalyst is $NiBr_2$ and an amount of said $NiBr_2$ is 0.001 to 0.04 mol as Ni to one mole of the carboxylic acid having a β-hydrogen atom or an anhydride thereof.

5. The method for producing an olefin according to claim 1, wherein said catalyst is a mixture of KBr and $[Rh(CO)_2Cl]_2$.

6. The method for producing an olefin according to claim 5, wherein an amount of said $[Rh(CO)_2Cl]_2$ is 0.00001 to 0.2 mol as Rh to one mole of the carboxylic acid having a β-hydrogen atom or an anhydride thereof.

7. The method for producing an olefin according to claim 5, wherein an amount of said $[Rh(CO)_2Cl]_2$ is 0.001 to 0.03 mol as Rh to one mole of the carboxylic acid having a β-hydrogen atom or an anhydride thereof.

8. The method for producing an olefin according to claim 5, wherein an amount of said KBr is 0.001 to 10 mol to one mole of said carboxylic acid having a β-hydrogen atom or an anhydride thereof.

9. The method for producing an olefin according to claim 5, wherein an amount of said KBr is 0.05 to 2 mol to one mole of said carboxylic acid having a β-hydrogen atom or an anhydride thereof.

10. The method for producing an olefin according to claim 1, wherein the catalyst further comprises an organophosphorous compound as a ligand compound.

11. The method for producing an olefin according to claim 10, wherein the content of the ligand compound is 0.3 to 100 mol to one mole of a metal atom of Group 8, Group 9, and Group 10 in said catalyst.

12. The method for producing an olefin according to claim 1, wherein the carboxylic acid having a β-hydrogen atom and the anhydride thereof are, respectively, represented by formula (i) and (ii):

wherein, $R^1$ represents a saturated or unsaturated hydrocarbon group having a β-hydrogen atom and 11 to 17 carbon atoms, and $R^2$ represents a hydrogen atom or a saturated or unsaturated hydrocarbon group having 1 to 17 carbon atoms.

13. The method for producing an olefin according to claim 1, wherein said converting is conducted in the presence of a solvent which is selected from the group consisting of an aromatic hydrocarbon, an aliphatic hydrocarbon, an alicyclic hydrocarbon, an alcohol, an ether, maleic anhydride, phthalic anhydride, acetic anhydride, and acetic acid.

14. The method for producing an olefin according to claim 13, wherein a weight ratio of a starting material/(a starting material+the solvent) is 1/26 to 1/1, wherein the starting material is the carboxylic acid having a β-hydrogen atom or an anhydride thereof.

15. The method for producing an olefin according to claim 2, wherein said catalyst is $RhBr_3$ and an amount of said $RhBr_3$ is 0.00001 to 0.2 mol as Rh to one mole of the carboxylic acid having a β-hydrogen atom or an anhydride thereof.

16. The method for producing an olefin according to claim 2, wherein said catalyst is $RhBr_3$ and an amount of said $RhBr_3$ is 0.001 to 0.04 mol as Rh to one mole of the carboxylic acid having a β-hydrogen atom or an anhydride thereof.

17. The method for producing an olefin according to claim 2, wherein said catalyst is $FeBr_2$ and an amount of said $FeBr_2$ is 0.00001 to 0.2 mol as Fe to one mole of the carboxylic acid having a β-hydrogen atom or an anhydride thereof.

18. The method for producing an olefin according to claim 2, wherein said catalyst is $FeBr_2$ and an amount of said $FeBr_2$ is 0.001 to 0.04 mol as Fe to one mole of the carboxylic acid having a β-hydrogen atom or an anhydride thereof.

19. The method for producing an olefin according to claim 1, wherein said catalyst is $[Rh(CO)_2Br]_2$.

* * * * *